United States Patent
De Lat et al.

(10) Patent No.: US 11,167,067 B2
(45) Date of Patent: Nov. 9, 2021

(54) BREAST PUMP AND METHOD FOR OPERATION

(71) Applicant: KONINKLIJKE PHILIPS N.V., Eindhoven (NL)

(72) Inventors: Bente De Lat, Eindhoven (NL); Arjan Teodor Van Wieringen, Eindhoven (NL); Arnold Aalders, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 245 days.

(21) Appl. No.: 16/079,305

(22) PCT Filed: Feb. 9, 2017

(86) PCT No.: PCT/EP2017/052854
§ 371 (c)(1),
(2) Date: Aug. 23, 2018

(87) PCT Pub. No.: WO2017/144282
PCT Pub. Date: Aug. 31, 2017

(65) Prior Publication Data
US 2019/0046700 A1  Feb. 14, 2019

(30) Foreign Application Priority Data
Feb. 24, 2016  (EP) ..................... 16157085

(51) Int. Cl.
*A61M 1/06* (2006.01)
*A61M 1/00* (2006.01)

(52) U.S. Cl.
CPC .............. *A61M 1/062* (2014.02); *A61M 1/06* (2013.01); *A61M 1/74* (2021.05); *A61M 1/75* (2021.05);
(Continued)

(58) Field of Classification Search
CPC .... A61M 1/062; A61M 1/064; A61M 1/0037; A61M 1/0005; A61M 1/0062; A61M 1/06; A61M 1/0031; A61M 1/0013; A61M 1/0041; A61M 2205/10; A61M 2205/50; A61M 1/007; A61M 1/066; A61M 1/068;
(Continued)

(56) References Cited

U.S. PATENT DOCUMENTS 5,810,772 A   9/1998   Niederberger
5,954,690 A   9/1999   Larsson
(Continued)

FOREIGN PATENT DOCUMENTS

DE   102014009056 A1   12/2014
WO   WO-2014037129 A1 *   3/2014   .......... A61M 1/0037
WO   WO-2016145173 A1 *   9/2016   ............ A61M 1/064

OTHER PUBLICATIONS

English Translation of DE102014009056 (Year: 2014).*

*Primary Examiner* — Kami A Bosworth

(57) ABSTRACT

The present invention relates to a breast pump (1) comprising a first pump (6) and second pump (6'), at least one expression kit (2, 2'), a valve assembly (13), and a control unit (8) for controlling the valve assembly (13) and/or the pumps (6, 6'), wherein the control unit (8) is configured to control the valve assembly (13) and/or the pumps (6, 6') for alternate operation of the first and second pumps (6, 6') in dependency of the operation times of the first and second pumps (6, 6').

18 Claims, 4 Drawing Sheets

(52) U.S. Cl.
CPC ..... *A61M 2205/10* (2013.01); *A61M 2205/50* (2013.01)

(58) Field of Classification Search
CPC .......... A61M 2210/1007; A61M 1/069; A61M 1/0693; A61M 1/06935
See application file for complete search history.

(56) References Cited

U.S. PATENT DOCUMENTS

| | | | |
|---|---|---|---|
| 6,355,012 B1 * | 3/2002 | Nuesch | A61M 1/06 604/119 |
| 6,673,036 B1 | 1/2004 | Britto | |
| 8,381,679 B2 | 2/2013 | Idensjoe | |
| 2008/0045887 A1 * | 2/2008 | Larsson | A61M 1/0072 604/74 |
| 2008/0063534 A1 | 3/2008 | Nakayama | |
| 2014/0031744 A1 | 1/2014 | Chen | |
| 2015/0112298 A1 * | 4/2015 | Pirzada | A61M 1/062 604/500 |
| 2015/0231316 A1 * | 8/2015 | Aalders | A61M 1/0035 604/74 |
| 2016/0287767 A1 * | 10/2016 | Simmons | A61M 1/062 |
| 2017/0173233 A1 * | 6/2017 | Tanaka | A61M 39/223 |
| 2017/0368244 A1 * | 12/2017 | Elad | A61M 1/064 |

\* cited by examiner

BREAST PUMP AND METHOD FOR OPERATION

This application is the U.S. National Phase application under 35 U.S.C. § 371 of International Application No. PCT/EP2017/052854, filed on Feb. 9, 2017, which claims the benefit of International Application No. 16157085.8 filed on Feb. 24, 2016. These applications are hereby incorporated by reference herein.

FIELD OF THE INVENTION

The present invention relates to breast pumps for extracting breast milk from a female breast and for a method of operating such a breast pump.

BACKGROUND OF THE INVENTION

In a breast pump according to DE 10 2014 009056 A1 with a controller, a drive motor, a drive transmission, two piston-cylinder units, two suction devices, each of which is attachable to a chest, and two pneumatic transfer lines, each of which connecting a piston-cylinder with a respective suction device, the drive transmission transmits a rotational movement of a shaft of the drive motor on the supply and return movements of the piston relative to the cylinders, so that periodic pressure variations on the transmission lines are transmitted to the suction devices. The two transmission lines are each provided with a vacuum relief valve adjustable by the controller and a pressure relief valve. By means of the valves it is possible to limit the pressure curves generated by the piston-cylinder units to desired ranges.

US 2014/0031744 A1 discloses a milk expressing device capable of simulating a baby's suckling. The device includes first and second vacuum sources, a throttle hole, a solenoid relief valve, first and second tubes, a breast shield, and a control circuit board. The first tube is connected to the first vacuum source. The breast shield is provided with the throttle hole to communicate with the atmosphere. When the first vacuum source is turned off, negative pressure in the first tube and the breast shield disappears slowly through the throttle hole. The second tube is connected to the second vacuum source. The breast shield is provided with the solenoid relief valve to communicate with the atmosphere. When the solenoid relief valve is activated, negative pressure in the second tube and in the breast shield is rapidly reduced. The control circuit board controls the first and second vacuum sources and the solenoid relief valve.

The expressing device according to the US 2014/0031744 A1 is only suitable for single side use. The user has to relocate the expression device from breast to breast. This is time-consuming and impractical. Besides, failure of one of the vacuum sources ends the lifetime of the whole device.

SUMMARY OF THE INVENTION

It is an object of the present invention to provide a breast pump capable of single and double side use to allow the user to decide depending on the circumstances and constitution to use the breast pump in the best suitable mode without overloading one of the pump units.

In a first aspect of the present invention a breast pump is presented, the breast pump comprising a first pump and a second pump, at least one expression kit, a valve assembly, and a control unit for controlling the valve assembly and/or the pumps, wherein the control unit is configured to control the valve assembly and/or the pumps for alternate operation of the first and second pumps in dependency of the operation times of the first and second pumps.

In a further aspect of the present invention a non-therapeutic method for operating a breast pump is presented, said breast pump comprising a first pump and a second pump, at least one expression kit, a valve assembly, and a control unit for controlling the valve assembly and/or the pumps, the method comprising the step of controlling the valve assembly and/or the pumps for alternate operation of the first and second pumps in dependency of the operation times of the first and second pumps.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed breast pump, in particular as defined in the dependent claims and as disclosed herein.

By way of monitoring the operation times of the pumps and controlling the valve assembly, respectively, the lifetime of the breast pump can be optimized even when the breast pump is used in single side mode. Wear of the pressure sources can be outbalanced and risk of premature failure can be reduced.

In an advantageous embodiment of the breast pump according to the present invention, a first expression kit and a second expression kit are provided. Thus, both single and double use mode are possible.

The control unit is preferably configured to control the valve assembly in order to control the difference in operation times of the first and second pumps, in particular such that their operation times are substantially equal. This provides the desired balance of the operation times of the pumps. Hereby, "substantially equal" shall be understood as meaning that the operation times do not differ by more than 50%, in particular by more than 25% or even more than 20%. In an embodiment, each time the breast pump is switched on, the pump having the lower number of operating hours is used for the next operation.

According to an embodiment of the breast pump according to the present invention, the valve assembly comprises a 4/2 valve with four ports and two settings. A 4/2 valve allows a compact design of the valve assembly.

In this embodiment, the first pump is connected to first and third pressure ports of the 4/2 valve and the second pump is connected to second and fourth pressure ports of the 4/2 valve.

Likewise, the first expression kit is connected to first and third work ports of the 4/2 valve and the second expression kit is connected to second and fourth work ports of the 4/2 valve.

Advantageously in a first setting of the 4/2 valve the first pump is connected to the first expression kit and the second pump is connected to the second expression kit, and that in a second setting of the 4/2 valve the first pump is connected to the second expression kit and the second pump is connected to the first expression kit. Switching between the two settings can easily be achieved by a control pulse from the control unit which is triggered by result of the comparison of the operation times.

According to another embodiment of the breast pump according to the present invention, the valve assembly comprises first and second 3/2 valves, wherein each of the 3/2 valves comprises three ports and two settings. 3/2 valves are cheaper than 4/2 valves. Besides, a failure of one of the valves can easily be repaired at low costs.

In this embodiment, the first pump is connected to first and second pressure ports of the first 3/2 valve and the second pump is connected to first and second pressure ports of the second 3/2 valve.

Likewise, the first expression kit is connected to a first work port of the first 3/2 valve and to a second work port of the second 3/2 valve and the second expression kit is connected to a second work port of the first 3/2 valve and to a first work port of the second 3/2 valve.

Advantageously in a first setting of the first and second 3/2 valves the first pump is connected to the first expression kit and the second pump is connected to the second expression kit, and in a second setting of the first and second 3/2 valves the first pump is connected to the second expression kit and the second pump is connected to the first expression kit. Switching between the pumps is again easily achieved by a control pulse from the control unit. Additionally, the two 3/2 valves allow coupling of the two pressure sources to alternatively strengthen or accelerate the resulting pressure. This allows either to accelerate the expression session or to apply higher pressure to increase the resulting milk volume.

According to yet another embodiment the valve assembly comprises first, second, third and fourth 2/2 valves, wherein each of the 2/2 valves comprises two ports and two settings. 2/2 valves are the easiest form of valves suitable for this application, they simply switch between open and closed positions simultaneously. Such valves are cheap, less prone to failure and easily changed if there is need.

In this embodiment, in a first setting the first pump is connected to a pressure port of the first 2/2 valve and to a blind port of the second 2/2 valve and the second pump is connected to a pressure port of the third 2/2 valve and to a blind port of the fourth 2/2 valve, and wherein the first expression kit is connected to a work port of the first 2/2 valve and the second expression kit is connected to a work port of the third 2/2 valve.

Likewise, in a second setting the first pump is connected to a pressure port of the second 2/2 valve and to a blind port of the first 2/2 valve and the second pump is connected to a pressure port of the fourth 2/2 valve and to a blind port of the third 2/2 valve, and wherein the first expression kit is connected to a work port of the fourth 2/2 valve and the second expression kit is connected to a work port of the second 2/2 valve.

According to an embodiment of the breast pump according to the present invention, the control unit comprises a recording unit for recording the operation time data of the first and second pumps, a storage for storing the operation time data, a processor for comparing and processing the operation time data and for selectively controlling the operation time of the first and second pumps. This setup needs only a few components which are common parts in electronics and thus widely available and easy to assemble. Failure of one of the components can be mended without much effort and also helps to prolong the lifetime of the breast pump.

The proposed method may further comprise one or more of the following steps:

i) recording the operation times of the first and second pumps,
ii) comparing the operation times of the first and second pumps,
iii) controlling the valve assembly (based on the information from steps i) and ii)) to alternately connect the first and second pumps the one or two expression kit that are actually used.

The control may be made such that the operation times of the first and second pumps are approximately equalized, wherein during an on-going use of one or more expression kit(s) it is preferably not switched between the pumps.

Controlling the operation times of the pumps by regular comparison of the operation times of the single pressure sources offers an easy way of prolonging the life time of the breast pump which is an expensive acquisition. The result of the comparison can be used to balance the operation times of the pumps by way of switching between the pumps by way of the valve assembly. This relieves the user from the necessity to manually switch the pressure sources in order to balance wear. The breast pump can be used without preparations or checks.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE EMBODIMENTS

Figure 1A:
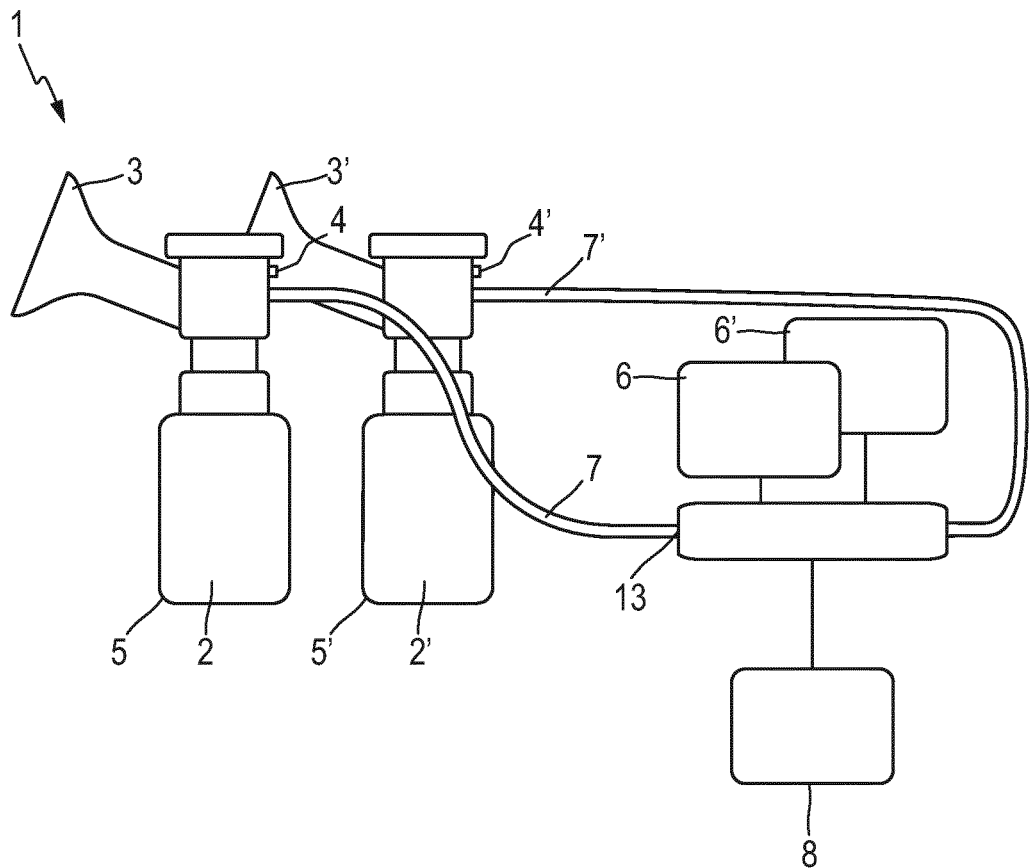
FIG. 1A shows a perspective schematic view of a breast pump generally suitable for incorporating the features of the invention.

FIG. 1A shows a schematic view of a breast pump 1 which is suitable for the implementation of the inventive features. The breast pump 1 comprises expression kits 2, 2' with funnels 3, 3' connected thereto. The funnels 3, 3' are shaped to receive a female breast therein and may be fabricated from any suitable resilient material like silicone or polyurethane. Containers 5, 5' are connected to the expression kits 2, 2' to receive the expressed breast milk therein. Alternatively, only one container 5 can be present which can be connected to both expression kits 2, 2' via e.g. fluid lines. The container 5, 5' can be connected to the expression kits 2, 2' for example by screwing or by a bayonet fixing. Venting valves 4, 4' can be provided in the expression kits 2, 2' for venting the components during and after expression. The expression kits 2, 2' are connected by pipes 7, 7' to a valve assembly 13. Respective vacuum pumps 6, 6' are connected to the valve assembly 13. The valve assembly 13 is designed to alternately connect the expression kits 2, 2' to the vacuum pumps 6, 6'. The valve assembly 13 and its functionality with respect to the alternate connection of the components of the breast pump 1 will be described in more detail with reference to FIGS. 2 to 4 below.

The valve assembly 13 is connected to a control unit 8. The control unit 8 is designed to control operation of the vacuum pumps 6, 6' depending on the operation time of each of the vacuum pumps 6, 6' to ensure maximum lifetime of the breast pump 1 due to uniform wear of the vacuum pumps 6, 6'. For this purpose, the control unit 8 may comprise, as shown in the embodiment depicted in FIG. 1C, a recoding unit 9 for recording the operation time data of the vacuum pumps 6, 6', a storage 10 for storing of the operation time data, and a processor 11 for comparing and processing the operation time data and for selectively controlling the operation time of the first and second vacuum pumps 6, 6'. This is achieved by controlling the valve assembly 13 in case only one expression kit 2, 2' is used. To prevent that only one vacuum pump 6, 6' is running in single-side use, the valve assembly 13 will be controlled to switch between the vacuum pumps 6, 6' to keep the operation times on an approximately even level. The control unit 8 further can comprise interface and/or activation means which are generally referred to by reference number 12.

Generally, double breast pumps 1 are very flexible in use. The double breast pump 1 can either be used for single use mode on one breast or in double use mode for two breasts simultaneously. The problem arising in single use mode however as mentioned above is the possible difference in operation times of the pumps 6, 6' with resulting differences in wear and different life times. The vacuum pumps 6, 6' are generally the most critical components in the breast pump 1 when it concerns lifetime and wear since the vacuum pumps 6, 6' are the most expensive parts thereof. When a breast pump 1 is at the end of its lifetime most often the vacuum pump 6, 6' itself or parts of the vacuum pump's 6, 6' driving system, especially the motor, will have failed. Therefore, the lifetime of the breast pump 1 is determined by the failure of one of the two vacuum pumps 6, 6'. In a consequence, the whole breast pump 1 has to undergo either expensive maintenance or even will be discarded completely by the user.

This problem will not arise when the breast pump 1 is always used in double use mode. However, not always the user is using both expression kits 2, 2' of the breast pump 1 simultaneously. It is very common that only one breast is expressed at a time. This will for example be the case when the user wants to avoid cleaning both expression kits 2, 2' or when the flow of milk is low. This can consequently lead to the use of one expression kit 2, 2' only (the second one might be disconnected and stored) and to unbalanced use of the two pumps 6, 6' in the double breast pump 1. The problem of unbalanced use especially occurs when each of the expression kits 2, 2' is fixedly connected to the respective vacuum pump 6, 6'. Thus, the system does not use its full lifetime potential if there is an unbalanced use of the vacuum pumps 6, 6'.

Figure 1C:
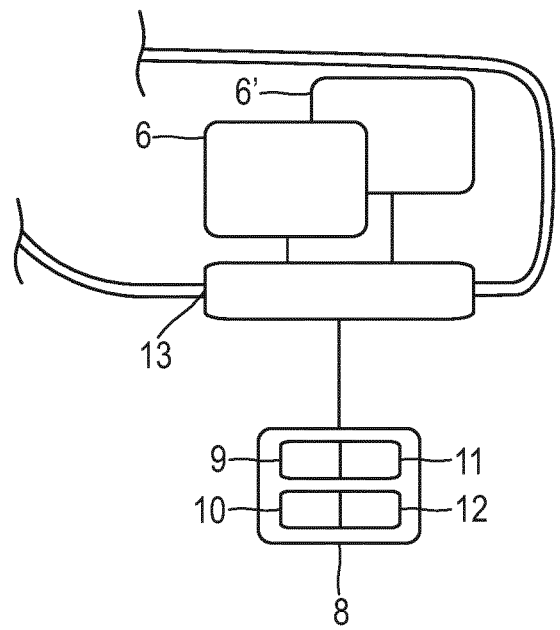
FIG. 1C shows a schematic embodiment of a control unit for a breast pump according to FIG. 1A or 1B.
Figure 1B:
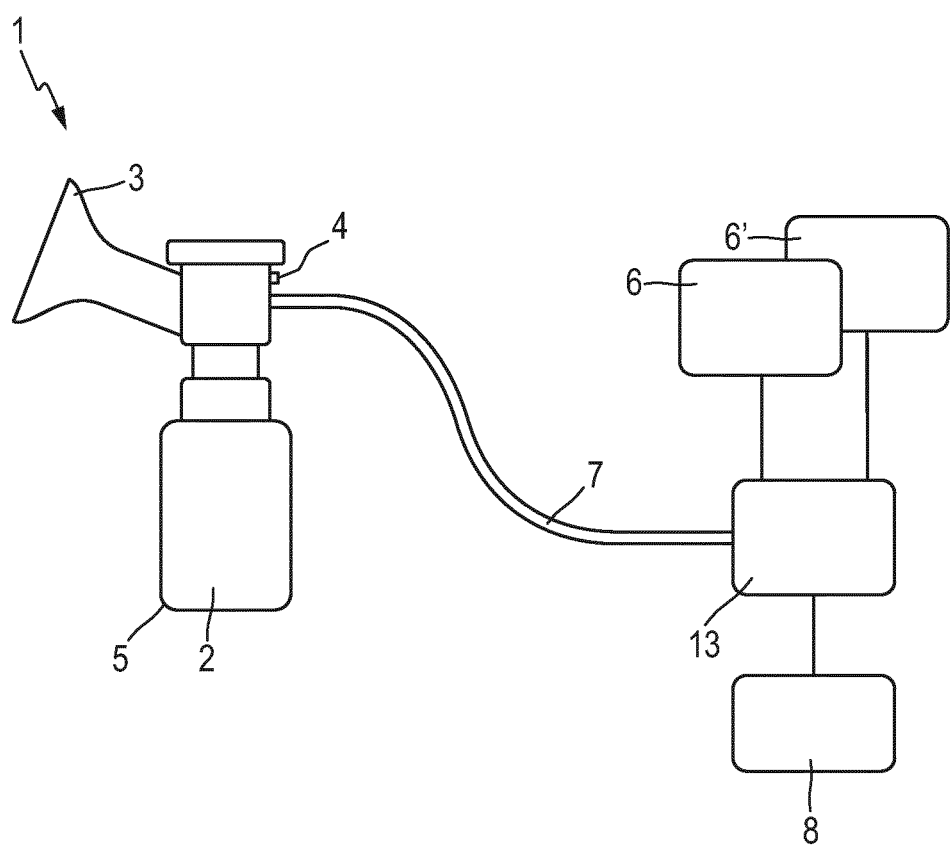
FIG. 1B shows a perspective view of another breast pump suitable for application of the invention.

For illustration purposes, FIG. 1B shows the breast pump 1 of FIG. 1A with one attached expression kit 2 only. This is for example useful when the user is traveling and doesn't want to carry the full set. The second expression kit 2' may be installed when appropriate.

In another version of the breast pump 1 shown in FIG. 1A the single expression kit 2 is connected separately to both vacuum pumps 6, 6' to have the possibility to generate variable combinations of suction frequency and vacuum strength to provide a more natural expression feeling. For example, one pump 6 can be used to generate a high vacuum with low suction frequency, and the other pump 6' can provide a lower vacuum at higher suction frequency. The latter configuration is known to stimulate milk flow. Likewise, if two expression kits 2, 2' are provided, both expression kits 2, 2' can be connected to both vacuum pumps 6, 6' by separate connections. Also in any of these embodiments the valve assembly 13 can be used to balance operation times of the vacuum pumps 6, 6' as described herein to maximize lifetime of the breast pump 1.

It would however very inconvenient for the user if a regular change of the vacuum pumps 6, 6' has to be observed. A lactating woman will not pay much attention to balancing the operation times of the vacuum pumps 6, 6'. Thus, in an embodiment the invention proposes to observe the operation time of each vacuum pump 6, 6' and by use of the valve assembly 13 balance the operation times until they are approximately equal. This helps to maximize the lifetime of the total breast pump 1. For this purpose, the control unit 8 is equipped with a recording unit for the operation time data of the vacuum pumps 6, 6' and with a processor 11 which is adapted to compare the determined operation time values to each other and to respectively control the operation of the vacuum pumps 6, 6' via the valve assembly 13 to equalize the operation time of the pumps 6, 6'.

Preferably, the control unit 8 will select the vacuum pump 6 or 6' with the lower operation time before expression starts, and the selected pump 6 or 6' will not be switched during expression as this might result in a change in vacuum and consequently a reduced suction, being a possible source of irritation for the user. Switching of the pump 6, 6' can for example take place when the expression kit 2 is changed to the other breast.

Figure 2:
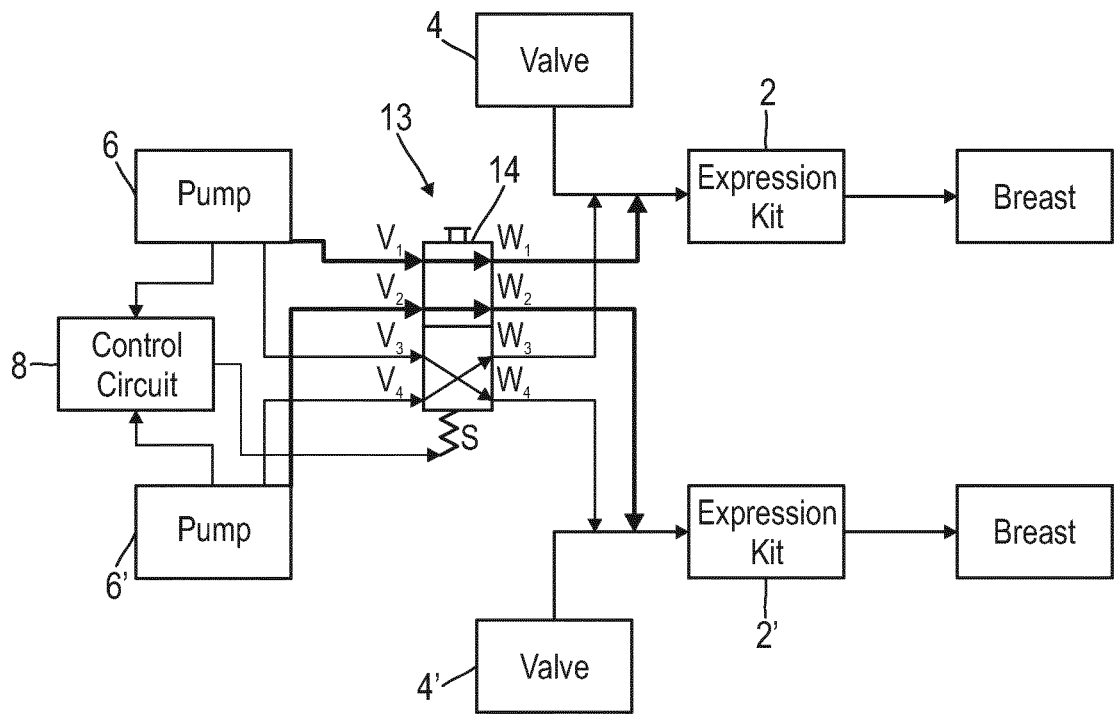
FIG. 2 shows a first schematic view of an embodiment of a breast pump according to the invention.
Figure 3:
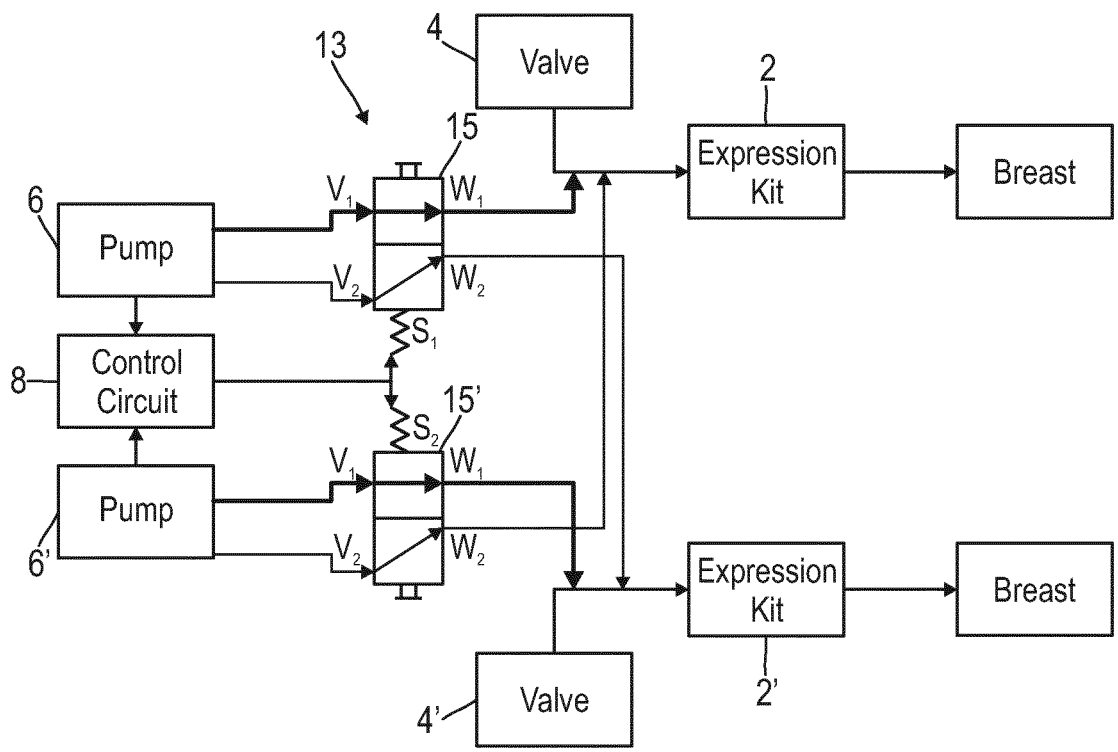
FIG. 3 shows a second schematic view of an embodiment of a breast pump according to the invention.
Figure 4:
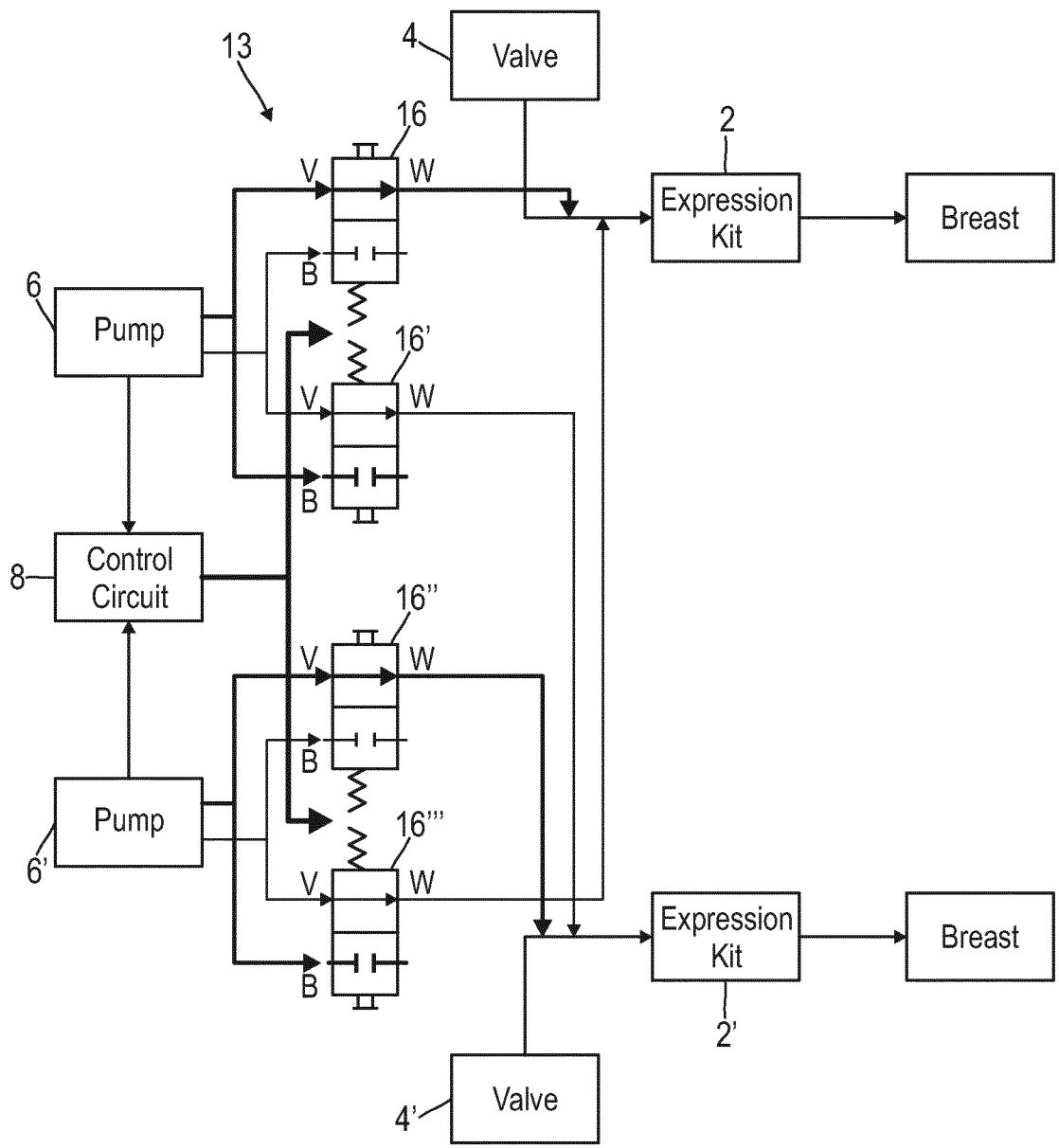
FIG. 4 shows a third schematic view of an embodiment of a breast pump according to the invention.

In the following three embodiments of breast pumps 1 with valve assemblies 13 suitable for this purpose are described in more detail. FIGS. 2 to 4 here are restricted to the main components which are necessary for the understanding of the inventive features. All other components have been omitted for the sake of clarity. The components not present in FIGS. 2 to 4 can for example be designed as shown in FIG. 1A, 1B or 1C or as known from common breast pumps known from the prior art.

In the first embodiment according to FIG. 2 the valve assembly 13 comprises one 4/2 valve 14. The 4/2 valve 14 comprises four ports and can be used in two different settings. The control unit 8 determines the operation times of the pumps 6, 6' in single use mode and controls the valve 14 to use either the first or the second setting, switching between the vacuum pumps 6, 6'. The breast pump 1 can then be used with one expression kit 2, 2' only without wearing out one of the vacuum pumps 6, 6' only. Switching allows reducing wear of the vacuum pumps 6, 6' by spreading the operation time to both vacuum pumps 6, 6'. In case the user is using both expression kits 2, 2' and accordingly both vacuum pumps 6, 6' in double use mode, the valve 14 is not powered. This ensures that the required power for the valve 14 is not adding to the power budget of the breast pump 1. In other words, power consumption of one vacuum pump 6, 6' in use plus power consumption of the valve 14 is less than the power consumption of two working vacuum pumps 6, 6'.

In FIG. 2, the first vacuum pump 6 is connected to first and third vacuum ports v1, v3 of the valve 14, and the second vacuum pump 6' is connected to second and fourth vacuum ports v2 and v4 of the valve 14. Likewise, the first expression kit 2 is connected to first and third work ports w1 and w3 of the valve 14 and the second expression kit 2' is connected to second and fourth work ports w2, w4 of the valve 14.

In the first setting of the valve 14 the first vacuum pump 6 is connected to the first expression kit 2 and the second vacuum pump 6' is connected to the second expression kit 6'. In the second setting, the first vacuum pump 6 is connected to the second expression kit 2' and the second vacuum pump 6' is connected to the first expression kit 2. The control unit 8 is connected to the pumps 6, 6' and by way of a steering port s to the valve 14. Switching between the first and second setting thus leads to changing the connections between the expression kits 2, 2' and the vacuum pumps 6, 6'. So when one of the expression kits 2, 2' is not used, deactivated or even disconnected, the control unit 8 causes the valve 14 to switch the vacuum pumps 6, 6' to alternately connect to the remaining one of the two expression kits 2, 2'.

Turning now to FIG. 3, a second embodiment of the invention is described. In the second embodiment, the valve assembly 13 comprises two 3/2 valves 15, 15'. The valves 15, 15' comprise each three ports and are operable in two settings each. Essentially, the functionality of the two valves 15, 15' is similar to the aforementioned 4/2 valve 14, but the 3/2 valves 15, 15' tend to be cheaper than the complex valve 14. The control unit 8 can in this embodiment control the two valves 15, 15' to switch from first to second setting and back. The valves 15, 15' are connected by way of steering ports s1 and s2 to the control unit 8. This system has also an additional benefit in the sense that it is possible to combine the two vacuum pumps 6, 6' to create a stronger and/or faster vacuum. This might be useful if expression has to take place in a limited time frame or when the milk flow is low.

In the embodiment in FIG. 3, the first vacuum pump 6 is connected to first and second vacuum ports v1, v2 of the first valve 15 and the second vacuum pump 6' is connected to first and second vacuum ports v1, v2 of the second valve 15'. Likewise, the first expression kit 2 is connected to a first work port w1 of the first valve 15 and to a second work port w2 of the second valve 15'. The second expression kit 2' is connected to a second work port w2 of the first valve 15 and to a first work port w1 of the second valve 15'.

In the first setting of the valves 15, 15' the first vacuum pump 6 is connected to the first expression kit 2 and the second vacuum pump 6' is connected to the second expression kit 2'. In the second setting of the valves 15, 15' the first vacuum pump 6 is connected to the second expression kit 2' and the second vacuum pump 6' is connected to the first expression kit 2. Thus again single use mode with one expression kit 2, 2' only can be used with the control unit 8 switching the vacuum pumps 6, 6' by way of the valves 15, 15' to ensure equal operation times of the vacuum pumps 6, 6'.

FIG. 4 shows a third embodiment of the invention comprising four 2/2 valves 16, 16', 16", 16'". In this system, the two vacuum pumps 6, 6' are connected via open/close valves 16, 16', 16", 16'" with both expression kits 2, 2'. The valves 16, 16', 16", 16'" will only switch at the same time in order to achieve the result of switching in single use mode the connection between the expression kit 2, 2' and the first or second vacuum pump 6, 6'.

In this embodiment, in a first setting the first vacuum pump 6 is connected to a vacuum port v of the first valve 16 and to a blind port b of the second valve 16'. The second vacuum pump 6' is connected to a vacuum port v of the third valve 16" and to a blind port b of the fourth valve 16'". Likewise in a second setting the first vacuum pump 6' is connected to a vacuum port v of the second valve 16' and to a blind port b of the first valve 16 and the second vacuum pump 6' is connected to a vacuum port v of the fourth valve 16'" and to a blind port b of the third valve 16".

This embodiment is possibly the cheapest one since the 2/2 valves 16, 16', 16", 16'" are very simple valves and thus not expensive. On the other hand, the manufacturing effort is higher due to many connections.

Aside from the ability to regulate the vacuum pump usage the valve assembly 13 according to the aforementioned embodiments also offers a diagnostic benefit with regard to the operation of the breast pump 1. When the vacuum system of the breast pump 1 is not working properly, e.g. vacuum is low or vacuum is not released, the valve assembly 13 can enable the control unit 8 to gather and interpret information about the status of the components. In case of low vacuum on one side, the valve assembly 13 for example can be used to check if one of the vacuum pumps 6, 6' is causing the low vacuum.

Although the embodiments described above comprise vacuum pumps 6, 6', vacuum ports, it should be understood that the claimed invention can also be implemented in a breast pump comprising sources of positive pressure, such as a positive displacement pump, as pumps, so as to simulate hand expression of the breast and baby suckling.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A breast pump comprising:
    a first pump and a second pump,
    at least one expression kit,
    a valve assembly, and
    a control unit configured to control at least one of the valve assembly and the first and second pumps for alternate operation of the first and second pumps to control a difference in operation times of the first and second pumps such that the operation times are substantially equal, whereby the control unit selects one of the first and second pumps having a lower recorded operation time prior to the start of an expression and maintains operation of the selected pump for a duration of the expression,
    wherein the control unit comprises a recording unit for recording operation time data of the first and second pumps, storage for storing the operation times data, and a processor for comparing and processing the recorded operation times data for the first and second pumps and for selectively controlling the operation times of the first and second pumps.

2. The breast pump according to claim 1, wherein the at least one expression kit comprises a first expression kit and a second expression kit.

3. The breast pump according to claim 2, wherein the valve assembly comprises a 4/2 valve with four ports and two settings and wherein the first expression kit is connected to first and third work ports of the four ports of the 4/2 valve and the second expression kit is connected to second and fourth work ports of the four ports of the 4/2 valve.

4. The breast pump according to claim 3,
wherein in a first setting of the two settings of the 4/2 valve, the first pump is connected to the first expression kit and the second pump is connected to the second expression kit, and
wherein in a second setting of the two settings of the 4/2 valve, the first pump is connected to the second expression kit and the second pump is connected to the first expression kit.

5. The breast pump according to claim 2, wherein the valve assembly comprises first and second 3/2 valves, wherein each of the first and second 3/2 valves comprises three ports and two settings.

6. The breast pump according to claim 5, wherein the first pump is connected to first and second ports of the three ports of the first 3/2 valve and the second pump is connected to first and second ports of the three ports of the second 3/2 valve.

7. The breast pump according to claim 5, wherein the first expression kit is connected to a first work port of the three ports of the first 3/2 valve and to a second work port of the three ports of the second 3/2 valve and the second expression kit is connected to a second work port of the three ports of the first 3/2 valve and to a first work port of the three ports of the second 3/2 valve.

8. The breast pump according to claim 7, wherein in a first setting of the two settings of the first and second 3/2 valves the first pump is connected to the first expression kit and the second pump is connected to the second expression kit, and wherein in a second setting of the two settings of the first and second 3/2 valves the first pump is connected to the second expression kit and the second pump is connected to the first expression kit.

9. The breast pump according to claim 2, wherein the valve assembly comprises first, second, third and fourth 2/2 valves, wherein each of the 2/2 valves comprises three ports and two settings.

10. The breast pump according to claim 9,
wherein in a first setting of the two settings of each 2/2 valve,
the first pump is connected to:
a pressure port of the three ports of the first 2/2 valve, and
a blind port of the three ports of the second 2/2 valve, and
the second pump is connected to:
a pressure port of the three ports of the third 2/2 valve, and
a blind port of the three ports of the fourth 2/2 valve, and
wherein in said first setting of the two settings,
the first expression kit is connected to a work port of the three ports of the first 2/2 valve, and
the second expression kit is connected to a work port of the three ports of the third 2/2 valve, and
wherein in a second setting of the two settings of each 2/2 valve,
the first pump is connected to:
a pressure port of the three ports of the second 2/2 valve, and
a blind port of the three ports of the first 2/2 valve, and
the second pump is connected to:
a pressure port of the three ports of the fourth 2/2 valve, and
a blind port of the two ports of the third 2/2 valve, and
wherein in said second setting of the two settings:
the first expression kit is connected to a work port of the three ports of the fourth 2/2 valve, and
the second expression kit is connected to a work port of the three ports of the second 2/2 valve.

11. The breast pump according to claim 1, wherein the control unit is configured to control the valve assembly in order to:
(1) control the difference in the operation times of the first and second pumps, and/or
(2) balance the operation times towards becoming substantially equal.

12. The breast pump according to claim 1, wherein the valve assembly comprises a 4/2 valve with four ports and two settings and wherein the first pump is connected to first and third ports of the four ports of the 4/2 valve and the second pump is connected to second and fourth ports of the four ports of the 4/2 valve.

13. A method for operating a breast pump, comprising:
controlling, by a control unit, at least one of a valve assembly and a first and a second pump for alternate operation of the first and second pumps to control a difference in operation times of the first and second pumps such that the operation times are substantially equal, whereby the control unit selects one of the first and second pumps having a lower recorded operation time prior to the start of an expression and maintains operation of the selected pump for aduration of the expression,
recording, by a recording unit, operation times data of the first and second pumps;
storing, in a storage unit, the recorded operation times data, and
comparing and processing, by a processor, the recorded operation times data for selectively controlling the operation times of the first and second pumps.

14. A breast pump comprising:
a first pump and a second pump,
at least one expression kit,
a valve assembly, and
a control unit,
wherein the control unit is configured and arranged to control the valve assembly and/or the first and second pumps for alternate operation of the first and second pumps to control a difference in operation times of the first and second pumps such that the operation times are substantially equal, whereby the control unit selects one of the first and second pumps having a lower recorded operation time prior to the start of an expression and maintains operation of the selected pump for a duration of the expression, and
wherein the valve assembly comprises a 4/2 valve with four ports and two settings, and
wherein the first pump is connected to first and third vacuum ports of the four ports of the 4/2 valve and the second pump is connected to second and fourth vacuum ports of the four ports of the 4/2 valve.

15. The breast pump according to claim 14, wherein the control unit is configured to control the valve assembly in order to control the difference in operation times of the first and second pumps to balance the operation times towards becoming substantially equal.

16. The breast pump according to claim 14, wherein the at least one expression kit comprises a first expression kit and a second expression kit.

17. The breast pump according to claim 16, wherein the first expression kit is connected to first and third work ports of the 4/2 valve and the second expression kit is connected to second and fourth work ports of the 4/2 valve.

18. A breast pump comprising:
a first pump and a second pump,
a first expression kit and a second expression kit, and
a valve assembly comprising first, second, third and fourth 2/2 valves, wherein each of the 2/2 valves comprises three ports and two settings,
a control unit,
wherein in a first setting of the two settings of each 2/2 valve,
the first pump is connected to:
a pressure port of the three ports of the first 2/2 valve, and
a blind port of the three ports of the second 2/2 valve, and
the second pump is connected to:
a pressure port of the three ports of the third 2/2 valve, and
a blind port of the three ports of the fourth 2/2 valve, and
wherein in said first setting of the two settings,
the first expression kit is connected to a work port of the three ports of the first 2/2 valve, and
the second expression kit is connected to a work port of the three ports of the third 2/2 valve, and
wherein in a second setting of the two settings of each 2/2 valve,
the first pump is connected to:
a pressure port of the three ports of the second 2/2 valve, and
a blind port of the three ports of the first 2/2 valve, and
the second pump is connected to:
a pressure port of the three ports of the fourth 2/2 valve, and
a blind port of the three ports of the third 2/2 valve,
wherein in said second setting of the two settings:
the first expression kit is connected to a work port of the three ports of the fourth 2/2 valve, and
the second expression kit is connected to a work port of the three ports of the second 2/2 valve.

* * * * *